United States Patent [19]

Leuenberger

[11] 4,355,931
[45] Oct. 26, 1982

[54] TAPPING DRILL

[76] Inventor: Roland Leuenberger, 15, Chemin de Bois de la Chappelle, 1213 Onex, Switzerland

[21] Appl. No.: 188,017

[22] Filed: Sep. 17, 1980

[30] Foreign Application Priority Data

Sep. 24, 1979 [FR] France .................. 79 24137

[51] Int. Cl.³ .................. B23B 45/12; A61B 17/16
[52] U.S. Cl. .................. 408/123; 128/92 E; 128/305.1; 192/43.2; 192/47; 408/122; 408/122.5; 408/139
[58] Field of Search .............. 128/92 EB, 92 E, 305.1, 128/317; 74/88, 89, 127; 192/43.2, 47; 408/5, 6, 17, 120, 121, 122, 123, 139, 122.5, 141, 142; 173/13; 81/58.4, 60

[56] References Cited

U.S. PATENT DOCUMENTS

| 260,359 | 7/1882 | Billings | 408/122 |
| 2,144,342 | 1/1939 | Morrison | 128/92 E |
| 2,439,803 | 4/1948 | Giesen | 128/92 E |
| 3,506,277 | 4/1970 | Harms | 279/1 |
| 4,111,208 | 9/1978 | Leuenberger | 128/305.1 |
| 4,124,026 | 11/1978 | Berner et al. | 128/92 E |

FOREIGN PATENT DOCUMENTS

| 2374886 | 7/1978 | France | 128/305.1 |
| 319607 | 2/1930 | United Kingdom | 74/359 |
| 751618 | 7/1956 | United Kingdom | 128/317 |
| 934284 | 8/1963 | United Kingdom | 192/103 B |

Primary Examiner—William R. Briggs
Assistant Examiner—Jerry Kearns
Attorney, Agent, or Firm—Michael N. Meller; Anthony H. Handal

[57] ABSTRACT

The tapping drill having a drive shaft driven with an alternating rotational movement, comprises, disposed between this drive shaft and the tool carrier, a ratchet mechanism capable, at will, of transforming the alternating rotational motion into a rotating movement by successive impulses in one direction or the other. The ratchet mechanism comprises a dog with spring extending through an annular member integral with the tool carrier, this dog bearing in an axial groove formed in an interior member integral with the drive shaft, in which interior member there can successively be distinguished three parts:

a first part comprising solely the groove;
a second part in which the groove is flanked by a cutaway on one side,
a third part in which the groove is flanked by a cutaway on the other side,
the dog being able to slide freely into the cut-aways and to be displaced along the groove. The dog is displaced along the groove by a control member bearing with play in an annular groove formed in the annular member.

13 Claims, 8 Drawing Figures

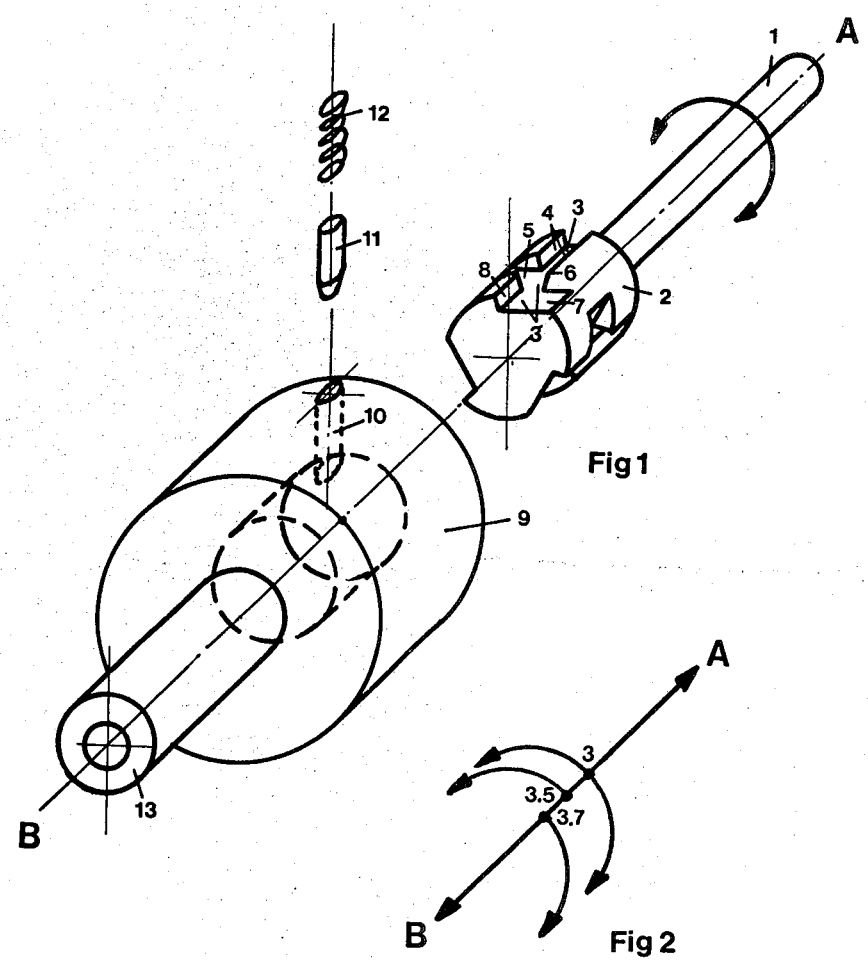

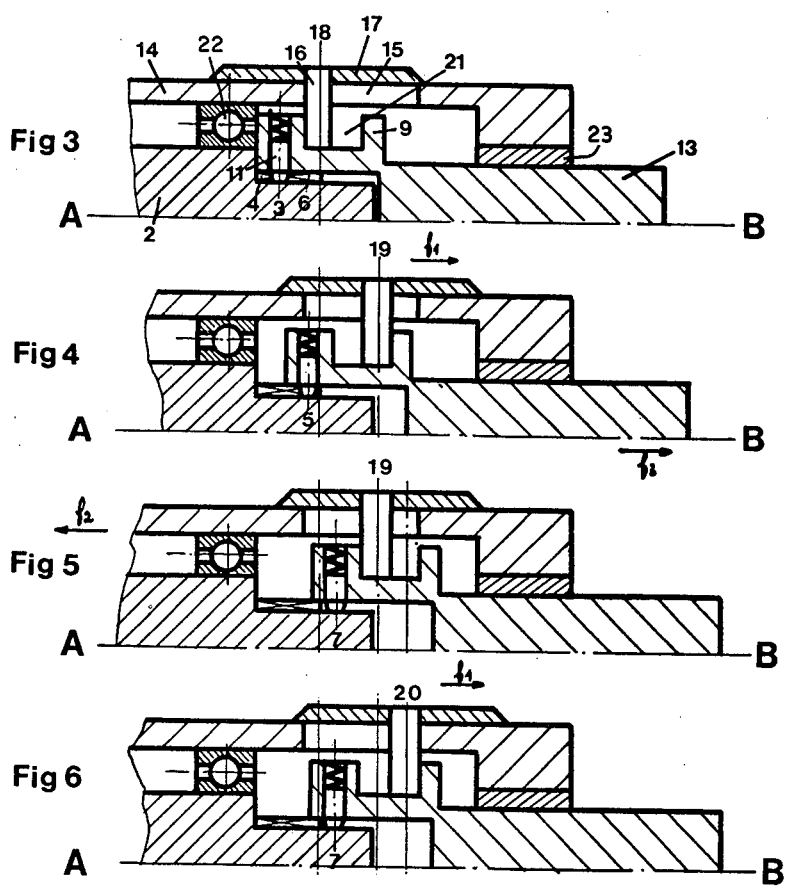
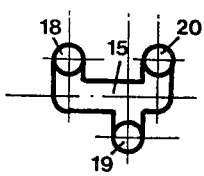
Fig 7

TAPPING DRILL

The present invention relates to a multi-purpose tapping drill which is of quite particular interest in surgery.

The need is known, for example in bone surgery, for drills having gentle movements of small amplitude, so as not to risk damaging adjacent tissues. One drill of this type, with alternating rotating movement, is described in Swiss Pat. No. 610,753. The operation of tapping is quite as delicate as the drilling operation, and for the lack of a device having sufficient safety, for the same reasons, surgeons have generally adopted the habit of tapping by hand. Thus the bringing on to the market of a tapping device possessing sufficient safeguards would respond to a real need.

The invention presents just such a tapping device which, by simple displacement of a control element, can also act as a drill. This tapping drill is moreover of general interest, by reason of the movement communicated to the tool, and contributes for example to safety in the building trade or in the factory, and to the prevention of amateur handicraft accidents.

The tapping drill according to the invention, in which the drive shaft is driven with alternating rotational motion, is characterized in that it comprises, disposed between the drive shaft and the tool, a ratchet mechanism capable of converting the alternating rotational motion at will into a rotating motion by successive impulses, in one direction or the other.

The accompanying drawing shows two forms of embodiment of the tapping drill given by way of example and a diagram of the principle of the involved movements. For clarity in the Figures only the references corresponding to new elements, from one Figure to the other, or necessary for explanation are carried forward from one Figure to the other beginning with FIG. 3.

FIG. 1 is an exploded perspective diagrammatic view of a simple form of embodiment.

FIG. 2 is specifically the diagram of principle of the movements.

FIGS. 3 to 6 are half-sections of a second, more elaborate, form of embodiment in the various possible configurations. In relation to FIG. 1, and although the two forms of embodiment are not identical, FIGS. 3 to 6 correspond to a sectional view from the rear of FIG. 1.

FIG. 7 is a top plan view of a groove with locking positions formed in the casing as represented in FIGS. 3 to 6.

Figure 8:
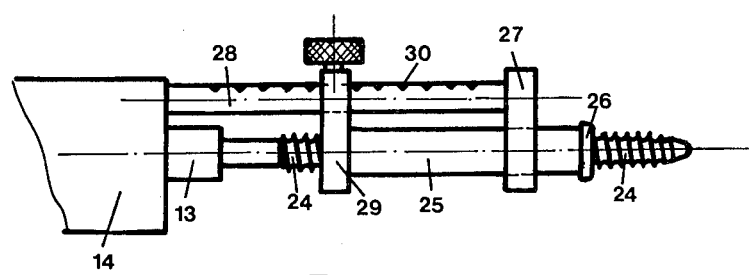
FIG. 8 is a left profile view of the tool carrier and casing.

In the simple form of embodiment as represented in FIG. 1 a drive element (not shown) is situated at top right, side A, and imparts an alternating rotating movement, as symbolized by the two-way arrow, to the drive shaft 1. A central piece 2 is integral with the drive shaft 1.

In this piece 2, three parts are distinguished in succession:

a first part having a groove 3, and only one groove 3; the flanks of this groove 3 are symbolized by 4;

a second part into which the groove 3 is prolonged but which is flanked by a cut-away 5 on one side; the single flank of the groove is symbolized by 6;

a third part into which the groove 3 is prolonged but which is flanked by a cut-away 7 on the other side; the single flank of the groove is symbolized by 8.

The second and third parts of the central piece 2 possess the characteristics of a cam and correspond to two juxtaposed cams of opposite directions.

An annular piece 9 integral with a tool-carrier 13, side B, is subject to the action of this central piece 2; this annular piece 9 possesses a radial bore 10 which receives a dog 11 equipped with a spring 12. This dog 11, bearing in the groove 3 of the central piece 2, acts as a pawl. The dog 11 can move along the groove 3 and slide freely into the cut-aways 5 and 7. The end of the dog 11 is preferably tapered and the groove 3 has a corresponding opening. The outer casing is not represented in FIG. 1.

It is easily understood that, according to the position of the dog 11 in the groove 3, the movement communicated to the tool-carrier 13 will be the same movement as that of the drive shaft 1, that is an alternating rotational movement, if the dog is in position 3 where it bears on the two flanks 4 of the groove 3, while the alternating rotational motion of the drive shaft will be transformed, upon the tool-carrier, into a rotating movement by successive impulses or surges in only one direction if the dog 11 is positioned in the groove 3 facing the cut-away 5 and thus bears only upon the flank 6. If the dog 11 is advanced by yet a further notch and is positioned in the groove 3 facing the cut-away 6, the movement communicated is a rotating movement by successive impulses or surges in the opposite direction.

All this is represented diagrammatically in FIG. 2 where the numerals 3, 3.5 and 3.7 respectively represent the positions of the dog 11 and the arrows translate the imparted movement.

In the other, more elaborate, form of embodiment represented in FIGS. 3 to 6 the drive shaft 1 (not shown) is placed to the left, on the side A, while the tool-carrier 13, represented without the lodgement for the tool, is placed to the right on the side B.

In these half-sections the annular piece 9 possesses an annular groove 21, the whole being surrounded by a casing 14 which is immobile and is in contact with the elements in motion through the intermediary of various bearings 22 and bushes 23.

This casing 14 comprises an axial groove 15 having three locking positions 18, 19 and 20, as represented in top plan view in FIG. 7. Through this groove 15 there extends a control member 16 fixed on an outer ring 17 and co-operating with the annular groove 21 formed in the annular piece 9. This control member 16 is capable of locking itself into the groove 15 in the position 18, 19 or 20.

In an advantageous variant which, as described below, permits reversal of the rotating movement in successive impulses simply by pushing or pulling upon the tapping drill, the distance between the first locking position 18, drive shaft side, and the second locking position 19 is equal to the travel of the pawl dog 11 in the groove 3 of the central piece 2; the distance between the second locking position 19 and the third locking position 20 is half of the distance between the first locking position 18 and the second locking position 19. These proportions are respected in FIG. 7.

With reference to the Figures, the tapping drill in succession performs the various functions of drilling by an alternating rotating movement, of screwing or tapping by a rotating movement by successive impulses in the screwing direction, of unscrewing or tap withdrawal by a similar movement in the opposite direction, and the passage from the "screwing" or "tapping" function to the "unscrewing" or "tap withdrawal" function being able to be carried out by a simple thrust upon the tapping drill, or withdrawal thereof.

In FIG. 3 the pawl dog 11 is in the groove 3 and comes to abut on each side on the flanks 4. Then the transmitted movement is that of the drive shaft, that is to say an alternating rotating motion. The control member 16 is in the locking position 18.

By displacement of the ring 17 in the direction of B as represented by the arrow $f_1$, the control member 16 comes to abut against the forward internal face of the groove 21, then continuing its travel to lock in the position 19, displaces the annular piece 9 and the tool-carrier 13, also the pawl dog 11 which comes into the position 5 of the groove 3. This dog 11 can now abut only upon the face 6 of the groove 3 and it is easily understood that the alternating rotational movement is "rectified" into a rotating movement in one direction, but by successive impulses. This configuration (FIG. 4) corresponds for example to the "tapping" or "screwing" function.

If now, without touching the ring 17, a withdrawal force towards A is exerted, as represented by the arrow $f_2$, one reaches the configuration as represented in FIG. 5. The control member 16 obviously has not shifted and has remained in its position 19. The tool, subjected to screwing and friction forces, has not shifted, and thus it is the assembly of drive shaft 1 and central piece 2 which has moved back. The pawl dog 11, without itself having shifted, is again situated in the position 7 of the groove 3 and can now abut only upon the flank 8 of this groove 3, which corresponds to a rotating movement by successive impulses opposite to the previous case. This configuration corresponds for example to the function "withdrawal of tap" or "unscrewing".

A simple thrust upon the tool in the direction of the arrow $f_3$ restores the configuration as represented in FIG. 4 and again reverses the rotating movement by successive impulses. The function "tapping" or "screwing" is restored.

Thus by simple pushing and withdrawal of the tool the rotating movements can be reversed.

It should be noted that in FIGS. 4 and 5, contrary to what really occurs, the elements which do not shift under the action of the forces $f_2$ and $f_3$ have been represented displaced, while the elements which shift under the action of the same forces $f_2$ and $f_3$ have been represented undisplaced. This representation, the converse of reality, permits of better understanding of the distance ratios between the successive positions of the pawl dog 11, namely 3, 3.5 and 3.7 respectively, and the locking positions 18, 19 and 20 of the control element 16.

In FIG. 6 the ring has been displaced in the direction of the arrow $f_1$ and the control member 16 has placed itself in the locking position 20. This configuration gives the same result as that represented in FIG. 5, for example the function "tap withdrawal" or "unscrewing", apart from the fact that the mechanism is locked and the movement can no longer be reversed by simple withdrawal of the tool.

In an advantageous form of embodiment the drive shaft transmits an alternating rotational motion of less than a half revolution, for example slightly more than 120°. The ratchet mechanism can then comprise one dog and a central piece which possesses three regularly disposed grooves per turn. As a preferred variant the ratchet mechanism comprises two dogs and the central piece comprises six regularly disposed grooves per turn.

Such a tapping drill can form an entity and be sold in its own right.

As variant it can comprise two parts which can be obtained separately:

a first part, acting as drive shaft, constituted by a drill with alternating rotational motion such as that described in Swiss Pat. No. 610,753, mentioned at the beginning of the description, a second part, adaptable to the first and serving as accessory, comprising the ratchet mechanism and the tool-carrier.

One particularly advantageous variant, especially for tapping (and screwing), corresponds to FIG. 8, where the tool-carrier 13 and the casing 14 (side B in FIGS. 3 to 6) are represented in profile view from the left. On the tool-carrier 13 there is mounted a tap 24 which extends through a hollow rod 25 terminated by a stop 26. This rod 25 is supported by a piece 27 through which it passes, and by a rod 28 fixed to the casing 14. Upon this same rod 25 there is fixed an element 29 which slides on the rod 28 and serves for the adjustment of the position of the stop 26, this adjustment being effected preferably by a ball (not shown) gripped in one of the impressions 30 of the rod 28. Thus the stop 26 is positioned, with reference to a graduated scale, in such manner as to permit the tap 24 to protrude by the length to be tapped.

Starting from the tapping position according to FIG. 4, it is seen that when the stop 26 is retained, the tap, continuing to advance in the threading which it has cut, draws the tool-carrier 13 forward and brings it into the position according to FIG. 5. The direction of rotation is reversed, the pawl dog 11 passing from the position 3.5 to 3.7. When this is done the tap now pushes back the tool-carrier 13 which returns into the position according to FIG. 4. The direction of rotation is reversed again, the pawl dog 11 coming back into the position 3.5, and so forth.

As a result the tap 24, in abutment, will commence to oscillate without damage to the threading and without exceeding the length fixed in advance by the adjusting element 29.

Thus there is complete safety.

I claim:

1. A tapping drill comprising:
   (a) a drive shaft;
   (b) means for imparting oscillating movement to said shaft around its longitudinal axis;
   (c) a tool carrier; and
   (d) a ratchet mechanism connecting said tool carrier to said shaft, wherein said ratchet mechanism comprises:
   (1) an interior drive member provided with a series of axially spaced successive lugs;
   (2) an exterior drive member attached to said interior member, and
   (3) means for selectively coupling said interior member with said exterior member through at least one of said lugs in order to transform the oscillating movement to a rotary movement by successive impulses in one direction or another at will.

2. The drill according to claim 1, wherein said interior member is integral with said drive shaft and has at least one axial groove; said exterior member is an annular member integral with said tool carrier and has a radial opening; and said rachet mechanism further comprises at least one dog disposed in said radial opening and bearing in said axial groove; said interior member being characterized by three parts:
- a first part comprising solely the groove;
- a second part comprising the groove flanked by a cut-away on one side; and
- a third part comprising the groove flanked by a cut-away on the other side;
- said dog being able to slide freely into said cut-aways and to be displaced along the groove.

3. The drill according to claim 2, wherein said dog has a tapered extremity and the interior member has one groove whose walls possess an equal angle of aperture.

4. The drill according to claim 2, wherein the cut-aways are shaped so that the amplitude of the alternating rotational motion imparted by the drive shaft is less than one half revolution.

5. The drill according to claim 4, wherein the cut-aways are shaped so that the amplitude is more than 120°; the ratchet mechanism comprises one dog; and the interior member has three regularly disposed grooves per turn.

6. The drill according to claim 4, wherein the cut-aways are shaped so that the amplitude is more than 120°; the ratchet mechanism comprises two dogs and the interior member has six regularly disposed grooves per turn.

7. The drill according to claim 2, further comprising a control member bearing with play in an annular groove formed in said annular member and adapted to displace said dog along said axial groove in said interior member.

8. The drill according to claim 7, further comprising a casing surrounding said ratchet mechanism and having an axial bore, a ring which slides on said casing, and wherein said control member is fixed on said ring and extends through said axial bore and comprising three locking positions.

9. The drill according to claim 8, wherein the distance between the first locking position, drive shaft side, and the second locking position is equal to the travel of the dog in the axial groove of the interior member.

10. The drill according to claim 9, wherein the distance between the second locking position and the third locking position is half of the distance between the first locking position and the second locking position.

11. The drill according to claim 8, wherein the drive shaft, the interior member, the ring carrying the control member, the annular member and the tool-carrier are coaxial, the dog being perpendicular to the axis.

12. The drill according to claim 8, further comprising a stop member integral with the casing.

13. The drill according to claim 12, wherein said stop member is adjustable in distance in relation to the casing.

* * * * *